United States Patent
Hershkowitz

(10) Patent No.: US 7,053,128 B2
(45) Date of Patent: May 30, 2006

(54) HYDROCARBON SYNTHESIS PROCESS USING PRESSURE SWING REFORMING

(75) Inventor: Frank Hershkowitz, Liberty Corner, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 171 days.

(21) Appl. No.: 10/756,651

(22) Filed: Jan. 13, 2004

(65) Prior Publication Data

US 2004/0170558 A1    Sep. 2, 2004

Related U.S. Application Data

(60) Provisional application No. 60/450,902, filed on Feb. 28, 2003.

(51) Int. Cl.
*C07C 27/00* (2006.01)

(52) U.S. Cl. ............... 518/700; 518/702; 518/703; 518/704; 518/726

(58) Field of Classification Search .............. 518/700, 518/702, 703, 704, 726
See application file for complete search history.

(56) References Cited

U.S. PATENT DOCUMENTS

| 6,495,610 B1 * | 12/2002 | Brown ................ 518/706 |
| 2001/0027220 A1 * | 10/2001 | Kennedy ............. 518/702 |
| 2002/0170228 A1 * | 11/2002 | Davis et al. ........... 44/300 |
| 2003/0235529 A1 * | 12/2003 | Hershkowitz et al. ..... 423/652 |

* cited by examiner

*Primary Examiner*—J. Parsa
(74) *Attorney, Agent, or Firm*—Paul E. Purwin

(57) ABSTRACT

The invention provides a method for producing liquid hydrocarbons by first generating in a pressure swing reformer a synthesis gas stream having a mole ratio of $H_2:CO$ greater than 2:1. Then, a portion of the hydrogen is separated to produce a synthesis gas stream having a mole ratio of $H_2:CO$ of about 2:1 which steam is then introduced into a hydrocarbon synthesis reactor for conversion to liquid products.

10 Claims, 5 Drawing Sheets

HYDROCARBON SYNTHESIS PROCESS USING PRESSURE SWING REFORMING

This application claims the benefit of U.S. Provisional Application No. 60/450,902 filed Feb. 28, 2003.

FIELD OF THE INVENTION

The present invention relates to process improvements in synthesizing hydrocarbon compounds from synthesis gas. More particularly, the invention relates to a process scheme wherein synthesis gas is produced in a cyclic packed-bed operation in which the reforming cycle of the synthesis gas production is performed at a higher pressure than the regeneration cycle and in which light gas and steam from the hydrocarbon synthesis process is used in the reforming cycle.

BACKGROUND OF THE INVENTION

Conventional synthesis gas generating processes include steam reforming, gas phase partial oxidation and autothermal reforming. Each of these processes has advantages and disadvantages when compared to each other.

In a steam reforming process, steam is reacted with a hydrocarbon containing feed to produce a hydrogen-rich synthesis gas. The general stoichiometry, as illustrated for methane, is:

$$CH_4 + H_2O > CO + 3H_2 \qquad (1)$$

Typically, an excess of steam is used to drive the equilibrium to the right. As applied to hydrogen manufacture, excess steam also serves to increase water gas shift:

$$CO + H_2O > CO_2 + H_2 \qquad (2)$$

Because of the high endothermicity of the reaction, steam reforming is typically carried out in large furnaces, in which the catalyst is packed into tubes. The tubes must withstand the high pressure of the produced synthesis gas, while transmitting heat at temperatures approaching 1000° C. As described in Stanford Research Institute International Report No. 148A (1995), steam reforming process efficiency, defined as the heat of combustion of product synthesis gas divided by the heat of combustion of reforming feed and furnace fuel, is approximately 79%, while the space velocity, defined as Standard Cubic Feet per Hour of $C_1$-equivalent feed/ft$^3$ of catalyst bed is 690 hr$^{-1}$. Unfortunately, steam reforming furnaces occupy a very large volume of space, orders of magnitude greater than the tube volume, such that low productivity limits the economic attractiveness of the process.

The gas phase partial oxidation process involves the partial oxidation of the hydrocarbon containing feed in the gas phase. The feed components are introduced at a burner where they combust with sub-stoichiometric oxygen to produce a synthesis gas mixture. The ideal gas phase partial oxidation reaction, as illustrated for methane, is:

$$CH_4 + \tfrac{1}{2}O_2 > CO + 2H_2 \qquad (3)$$

However, gas-phase reaction kinetics tend to over-oxidize some of the feed, resulting in excessive heat generation and substantial yield of $H_2O$, $CO_2$, and unreacted hydrocarbons that my leave the reactor as soot.

For these reasons, when gas phase partial oxidation chemistry is applied to clean feeds, it is preferred to add steam to the feed and add a bed of steam reforming catalyst to the bottom of the gas phase partial oxidation reactor vessel. This combination of gas phase partial oxidation and steam reforming is called autothermal reforming. The heat needed for steam reforming is provided in-situ from the excess heat generated by the gas phase partial oxidation reactions.

Autothermal reforming can be substantially more compact than steam reforming because furnaces are not used to provide heat of reaction. Embodiments of autothermal reforming presently under development for gasoline-powered fuel cell vehicles make use of a catalytic partial oxidation step, which can impart even greater compactness to the autothermal reforming process. The thermal efficiency of autothermal reforming reactors are generally in the range of 90%. While autothermal reforming based on catalytic partial oxidation may have high productivity (gas hourly space velocity on order of $10^4$ as $C_1$-equiv.), conventional partial oxidation-based autothermal reforming has a space velocity very similar to that of steam reforming (about $10^3$ hr$^{-1}$). However, autothermal reforming requires a source of oxygen. In the fuel cell vehicle case, this oxygen in typically provided as low-pressure air, which results in a nitrogen-diluted, low-pressure synthesis gas, while in refinery or chemicals embodiments, this oxygen is typically provided as purified $O_2$, and the cost of air separation can be greater than the cost of the autothermal reforming process.

Sederquist (U.S. Pat. Nos. 4,200,682, 4,240,805, 4,293, 315, 4,642,272 and 4,816,353) teaches a steam reforming process in which the heat of reforming is provided within the bed by cycling between combustion and reforming stages of a cycle. As described by Sederquist, the high quality of heat recovery within the reforming bed results in a theoretical efficiency of about 97%. However, the examples and commercial projections within these patents describe a process that operates at very low productivity, with space velocities of around 95 hr$^{-1}$ (as $C_1$-equiv). Moreover, this process requires a compressor to compress the product synthesis gas to useful pressures for hydrocarbon synthesis.

Recently a highly efficient and highly productive process for producing synthesis gas in a cyclic, packed-bed operation has been discovered. In this process, the reforming step involves preheating a first zone to a temperature in the range of about 700° C. to 2000° C. and then introducing a 20° C. to 600° C. hydrocarbon-containing feed, along with steam and optionally $CO_2$ to the inlet of the first zone. Upon introduction of the reactants, the hydrocarbon is reformed into synthesis gas over a catalyst in this first zone. The synthesis gas is then passed from the first zone to a second zone, where the gas is cooled to a temperature close to the inlet temperature of the hydrocarbon feed. The synthesis gas is recovered as it exits the inlet of the second zone.

The regeneration step begins when a gas is introduced to the inlet of the second zone. This gas is heated by the stored heat of the second zone to the high temperature of the zone and carries the heat back into the first zone. Finally, an oxygen-containing gas and fuel are combusted near the interface of the two zones, producing a hot flue gas that travels across the first zone, thus re-heating that zone to a temperature high enough to reform the feed. Once heat regeneration is completed, the cycle is completed and reforming begins again.

An advantage of this process is the ability to operate the reforming step at a higher pressure than the regeneration step, thus creating a pressure swing, and producing high pressure synthesis gas.

Processes for producing liquid and gaseous hydrocarbon products from synthesis gas are known. These include Fischer-Tropsch synthesis, methanol synthesis and hydroformylation. Each of these are exothermic processes that operate best at a $H_2$:CO molar ratio of about 2.

Fischer-Tropsch synthesis typically is carried out using a cobalt or iron catalyst at temperatures of between 200° C. to 450° C. and pressures of between 10 and 300 atmospheres. The hydrocarbon product is roughly equivalent to a very paraffinic, natural petroleum oil that contains predominantly straight chain, saturated paraffins, some olefins and less than about 1% alcohols, fatty acids and other oxygenates.

Methanol synthesis typically is carried out using copper-zinc oxide-alumina catalysts at pressures of about 50–100 atm. and temperatures of about is 200° C.–300° C. The by-products of methanol synthesis includes ethers, formates, ketones, hydrocarbons, and higher alcohols.

Hydroformylation involves the reaction of olefins with CO and $H_2$ and typically is carried out in the liquid phase in the presence of a metal carbonyl catalyst at temperatures in the range of 50° C. to 200° C. at pressures of 10 to 200 atm.

The practical application of any synthesis gas production technique or hydrocarbon conversion process will depend upon how well the upstream and downstream processing systems can be integrated into an overall process design. The invention described below and defined in the claims addresses practical process design and operating requirements that achieve effective integration of pressure swing reforming with downstream hydrocarbon conversion and that provides unanticipated advantages.

SUMMARY OF THE INVENTION

The present invention, in one aspect, provides an improvement in exothermic hydrocarbon synthesis processes that use synthesis gas, in which the improvement comprises integrating pressure swing reforming with such a synthesis process whereby thermal and material efficiencies over conventional reforming are achieved. Thus is one embodiment at least some hydrogen which is produced in the pressure swing reforming process is removed from the synthesis gas and is combusted with air to provide the heat for the regeneration step of the pressure swing reforming process. In another embodiment the exothermic synthesis process is cooled with water to produce steam which is used in the pressure swing reforming.

A preferred embodiment of the invention comprises:

(a) introducing a feed stream comprising a hydrocarbon and steam through a first end of a first zone containing bed packing materials and a steam reforming catalyst to produce at a first pressure a product synthesis gas stream containing a ratio of $H_2$:CO greater than 2:1, (b) passing at least a portion of the product to step (a) to a second zone containing bed packing materials, and transferring the sensible heat from the product to the packing materials;

(c) removing substantially all of the product from said second zone;

(d) introducing an oxygen-containing gas into a second end of said second zone;

(e) contacting said oxygen-containing gas with a fuel and combusting said gas and fuel within said zones at a second pressure lower than the first pressure, thereby re-heating said first zone to reforming temperatures and creating a fluegas which exits through the first end of said first zone;

(f) separating sufficient hydrogen from the product recovered in step (c) to produce a synthesis gas stream having a $H_2$:CO ratio of about 2:1;

(g) using separated hydrogen of step (b) as fuel in step (e); and (h) introducing the synthesis gas of step (f) into a hydrocarbon synthesis reactor for conversion therein to liquid products.

The embodiments of the invention are set forth in the detailed description hereinafter.

DETAILED DESCRIPTION

Figure 1A:
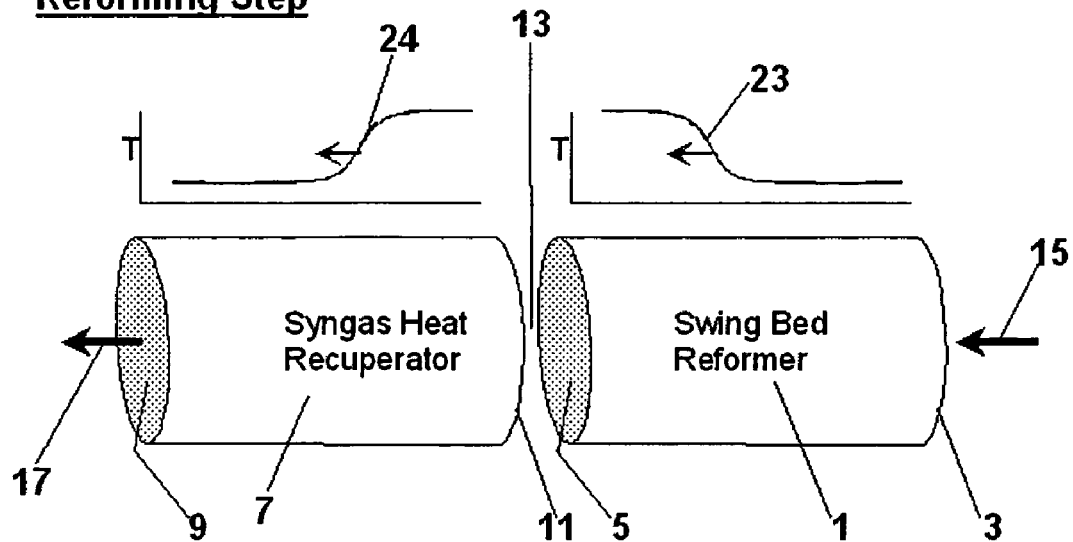
FIGS. 1a and 1b are schematic illustrations showing the basic reforming and regeneration steps of pressure swing reforming.
Figure 1B:
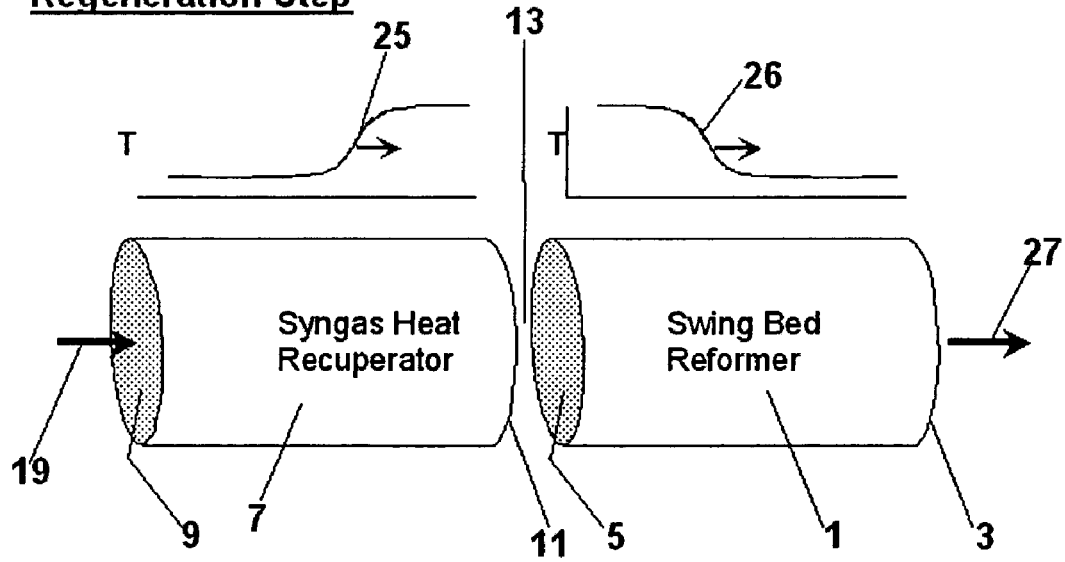

The basic two-step cycle of pressure swing reforming is depicted in FIG. 1. Referring now to FIGS. 1a and 1b, a first zone, or reforming zone (1), called a swing bed reformer, and a second zone, or recuperating zone, called a synthesis gas heat recuperator (7). The beds of both zones will include packing material, while the reforming bed (1) will include catalyst for steam reforming. Though illustrated as separate reforming and recuperating zones, it is to be recognized that the pressure swing reforming apparatus may comprise a single reactor.

As shown in FIG. 1a, at the beginning of the first step of the cycle, also called the reforming step, the reforming zone (1) is at an elevated temperature and the recuperating zone (7) is at a lower temperature than the reforming zone (1). A hydrocarbon-containing feed is introduced via a conduit (15), into a first end (3) of the reforming zone (1) along with steam. The hydrocarbon may be any material that undergoes the endothermic steam reforming reaction including methane, petroleum gases, petroleum distillates, kerosene, jet fuel, fuel oil, heating oil, diesel fuel and gas oil and gasoline. Preferably the hydrocarbon will be a gaseous material comprising methane and other normally-vapor phase hydrocarbons. Preferably, the steam will be present in proportion to the hydrocarbon in an amount that results in a steam to carbon ratio between about 1 and about 3 (considering only carbon in the hydrocarbon, not carbon in CO or $CO_2$ species that may be present).

This feed stream picks up heat from the bed and is converted over the catalyst and heat to synthesis gas. As this step proceeds, a temperature profile (23) is created based on the heat transfer properties of the system. When the bed is designed with adequate heat transfer capability, as described herein, this profile has a relatively sharp temperature gradient, which gradient will move across the reforming zone (1) as the step proceeds.

Synthesis gas exits the reforming bed (1) through a second end (5) at an elevated temperature and passes through the recuperating zone (7), entering through a first end (11) and exiting at a second end (9). The recuperating zone (7) is initially at a lower temperature than the reforming zone (1). As the synthesis gas passes through the recuperating zone (7), the synthesis gas is cooled to a temperature approaching the temperature of the zone substantially at the second end (9), which is approximately the same temperature as the regeneration feed introduced during the second step of the cycle via conduit (19) (e.g. from about 20° C. to about 600° C.). As the synthesis gas is cooled in the recuperating zone (7), a temperature gradient (24) is created and moves across the recuperating zone (7) during this step.

At the point between steps, the temperature gradients have moved substantially across the reforming zone (1) and the recuperating zone (7). The zones are sized so that the gradients move across both in comparable time during the above reforming step. The recuperating zone (7) is now at the high temperature and the reforming zone (1) is at low temperature, except for the temperature gradient that exists near the exits of the respective zones. The temperature of the reforming zone (1) near the inlet end (3) has now been cooled to a temperature that approaches the temperature of the hydrocarbon feed that has been entering via conduit (15) (e.g. from about 20° C. to about 600° C.).

In the practice of pressure swing reforming, there are alternative means for determining the end of the reforming step. Toward the end of the reforming step, the temperature at end (5) of the reforming zone is reduced and consequently the reforming performance deteriorates below acceptable conversion efficiencies. Reforming performance, as used herein, refers to the conversion of feed hydrocarbons into synthesis gas components of $H_2$, CO and $CO_2$. The term percent conversion, as used herein, is calculated as the percent conversion of the carbon in feed hydrocarbonaceous species into synthesis gas species of CO and $CO_2$. The term unconverted product hydrocarbons, as used herein, refers to product hydrocarbonaceous species that are not synthesis gas components of $H_2$, CO and $CO_2$. These typically include product methane, as well as feed hydrocarbons and the cracking products of feed hydrocarbons. The reforming step ends when the reforming performance deteriorates to a level that is below acceptable limits. In practice, optimization of the overall reforming and synthesis gas utilization process will dictate a desired, time-averaged level of reforming conversion. That time-averaged level of reforming conversion is typically greater than 80%, preferably greater than 90%, and most preferably greater than 95%.

The point in time at which the reforming step is ended, and thus the duration of the reforming step, may be chosen (a) as a response to the time-varying performance of the reformer during each reforming step; or (b) based on overall (time-averaged) performance or the system; or (c) fixed as a constant reforming step duration. In embodiment (a), at least one feature of the operation is monitored that is correlated to the reforming performance. This feature may be a composition such as $CH_4$, $H_2$, or CO, or alternatively a temperature, such as the temperature at the end (5) of the reforming bed. In one embodiment of the present invention, the reforming step is ended when the temperature at the end (5) of the reforming has decreased to a pre-selected temperature between about 700° C. and about 1200° C. In embodiment (b), the reforming step duration is adjusted based on a measured feature that reflects the overall (time-averaged) performance or the system. This may be an average product composition such as $CH_4$, $H_2$, or CO. In one embodiment the present invention, the reforming step duration is adjusted based on the time-averaged concentration of $CH_4$ in the product, using control strategies known in the art to shorten or lengthen the duration to achieve a predetermined target $CH_4$ amount. In a preferred embodiment, the target $CH_4$ amount is set at an amount that represents between about 1% and about 15% of the hydrocarbonaceous feed carbon. In case (c), the reforming step duration is of fixed length, at a value that is predetermined to be acceptable for the space velocity of the operation. In one embodiment the present invention, the reforming step duration is fixed at a duration between about 0.1 sec and less than about 60 seconds and preferably between about 1.0 and 30 seconds.

After the synthesis gas is collected via an exit conduit (17) at the second end (9) of the recuperating zone (7), the second step of the cycle, also called the regeneration step begins. The regeneration step, illustrated in FIG. 1b, basically involves transferring the heat from the recuperator bed (7) to the reformer bed (1). In so doing, the temperature gradients 25 and 26 move across the beds similar to but in opposite directions to gradients 23 and 24 during reforming. In a preferred embodiment, an oxygen-containing gas and fuel are introduced via a conduit (19) into the second end (9) of the recuperating zone (7). This mixture flows across the recuperating zone (7) and combusts substantially at the interface (13) of the two zones (1) and (7). In the present invention, the combustion occurs at a region proximate to the interface (13) of the recuperation zone (7) and the reforming zone (1). The term, "region proximate", in the present invention, means the region of the PSR beds in which regeneration step combustion will achieve the following two objectives: (a) the heating of the reforming zone such that end (5) of the reforming zone is at a temperature of at least 800° C., and preferably at least 1000° C. at the end of the regeneration step; and (b) the cooling of the recuperation zone to a sufficient degree that it can perform its function of accepting synthesis gas sensible heat in the subsequent reforming step. Depending on specific regeneration embodiments described herein, the region proximate to the interface can include from 0% to about 50% of the volume of the recuperation zone (7), and can include from 0% to about 50% of the volume of the reforming zone (1). In a preferred embodiment of the present invention, greater than 90% of the regeneration step combustion occurs in a region proximate to the interface, the volume of which region includes less than about 20% the volume of the recuperating zone (7) and less than about 20% the volume of reforming zone (1).

The location of combustion may be fixed by introduction of one of the combustion components, e.g., the fuel, at or substantially at, the interface of the two zones (13), while the other component, e.g., the oxygen-containing gas may be introduced at the first end (9) of the recuperating zone (7). Alternatively, the fuel and oxygen-containing gas (19) streams may be mixed at the open-end (9) of the recuperating zone (7) and travel through the zone and combust at the interface of the zones (13). In this embodiment, the location of combustion is controlled by a combination of temperature, time, fluid dynamics and catalysis. Fuel and oxygen conventionally require a temperature-dependent autoignition time to combust. In one embodiment, the flow of a non-combusting mixture in a first substep of regeneration will set the temperature profile in the recuperating zone (7) such that the zone is not hot enough to ignite until the mixture reaches the interface of the zones.

The presence of catalyst in the reforming zone can also be used to initiate combustion at that location, and a space between the reforming and recuperating zones can be added and designed to further stabilize the combustion process and confine the combustion to the area proximate to the above described interface. In yet another embodiment, the location of combustion is fixed by mechanical design of the recuperating zone. In this design, the fuel and oxygen-containing gas are travelling in separate channels (not shown), which prevent combustion until the feeds combine at the interface of the zones (13). At that location, flame holders (not shown) or a catalyst in the reforming zone will ensure that the combustion occurs.

The combustion of the fuel and oxygen-containing gas creates a hot fluegas that heats the reforming zone (1) as the flue gas travels across that zone. The fluegas then exits through the first end of the reforming zone (3) via a conduit (27). The composition of the oxygen-containing gas/fuel mixture is adjusted to provide the desired temperature of the reforming zone. The composition and hence temperature is adjusted by means of the proportion of combustible to non-combustible portions of the mixture. For example, non-combustible gases such as $H_2O$, $CO_2$, and $N_2$ can be added to the mixture to reduce combustion temperature. In a preferred embodiment, non-combustible gases are obtained by use of steam, flue gas, or oxygen-depleted air as one component of the mixture. When the hot fluegas reaches the temperature gradient within the reformer, the gradient moves further across the bed. The outlet temperature of the fluegas will be substantially equal to the temperature of the reforming zone (1) near the inlet end (3). At the beginning of the regeneration step, this outlet temperature will be substantially equal to the inlet temperature of the reforming feed of the preceding, reforming, step. As the regeneration step proceeds, this outlet temperature will increase slowly and then rapidly as the temperature gradient reaches end (3), and can be 50–500° C. above the temperature of the reforming feed by the end of the step.

In the practice of pressure swing reforming, there are alternative means for determining the end of the regeneration step. The regeneration step ends when sufficient heat has been supplied or conveyed to the reforming bed to enable the carrying out of the reforming step. The point in time at which the regeneration step is ended, and thus the duration of the regeneration step, may be chosen (a) as a response to the time-varying performance of the PSR during each regeneration step; or (b) based on overall (time-averaged) performance or the system; or (c) fixed as a constant regeneration step duration. In embodiment (a), some feature of the operation is monitored that is related to the regeneration performance. This feature could be a composition such as $O_2$, $CH_4$, $H_2$, or CO, or could be a temperature such as the temperature at the end (3) of the reforming bed. In one embodiment of the present invention, the regeneration step is ended when the temperature at the end (3) of the reforming bed has increased to a pre-selected temperature between about 200° C. and about 800° C. In embodiment (b), the regeneration step duration is adjusted based on a measured feature that reflects the overall (time-averaged) performance of the system. This feature may be an average product composition such as $CH_4$, $H_2$, or CO, or some other system measurement. In one embodiment of the present invention, the regeneration step duration is adjusted based on the time-averaged concentration of $CH_4$ in the product, using control strategies known in the art to shorten or lengthen the duration to achieve the target $CH_4$ amount. In a preferred embodiment, the target $CH_4$ amount is set at an amount that represents between about 1% and about 15% of the hydrocarbonaceous feed carbon. In embodiment (c), the regeneration step duration is of fixed length, at a value that is predetermined to be acceptable for the space velocity of the operation. In one embodiment the present invention, the regeneration step duration is fixed at a duration between about 0.1 second and about 60 seconds and preferably 1.0–30 seconds. In all of these cases, but particularly in embodiment (c), it is preferable to also adjust the regeneration flow rates to increase or decrease the amount of heat added to the bed during the step—in a manner similar to that described with respect to adjustment of duration in embodiment (b), above. In a further embodiment of the present invention, the regeneration step duration is fixed at a duration between about 1 second and about 60 seconds, and the regeneration flow rate is adjusted over time so that the time-average concentration of CH4 in the reforming product approaches a target $CH_4$ amount that is set at an amount that represents between about 1% and about 15% of the hydrocarbonaceous feed carbon.

The reforming zone is now, once again, at reforming temperatures suitable for catalytic reforming.

In the practice of the present invention it is important to operate the two steps of the cycle at different pressures. This is advantageous because it is costly to compress air to high pressure, while it is desirable to have synthesis gas at high pressure. Thus, in a preferred embodiment, the reforming step is carried out at higher pressures than the regeneration step. The pressure swing is enabled because of the large volumetric heat capacity difference between the solid and the gas.

Pressure swing reforming operating temperatures and pressures are given in Table 1.

TABLE 1

|  | Broad Range | Preferred Range |
| --- | --- | --- |
| Reforming Step Pressure | 2–100 atm | 5–50 atm |
| Regeneration Step Pressure | 1–20 atm | 1–10 atm |
| Reforming Feed Temperature | 20–600° C. | 150–450° C. |
| Regeneration Feed Temperature | 20–600° C. | 150–450° C. |
| Regeneration Peak Bed Temperature | 700–2000° C. | 900–1600° C. |

The space velocity of a system is typically expressed on an hourly basis as the standard volumetric gas flow rate of feed divided by the volume of catalyst bed, called gaseous hourly space velocity, or GHSV. Space velocity can also be defined in terms of the hydrocarbon component of feed. As so defined, the GHSV for a methane feed would be the standard hourly volumetric gas flow rate of methane divided by the bed volume. As used herein, the term space velocity, abbreviated as $C_1GHSV$, refers to the space velocity of any hydrocarbon feed placed on a $C_1$ basis. As such, the hydrocarbon feed rate is calculated as a molar rate of carbon feed, and standard volume rate calculated as if carbon is a gaseous species. For example, a gasoline feed having an average carbon number of 7.0 that is flowing at a gaseous flow rate of 1,000 NL/hr into a 1.0 L bed would be said to have a space velocity of 7,000. This definition is based on feed flow during the reforming step and wherein the bed volume includes all catalysts and heat transfer solids in the reforming and recuperating zones.

In pressure swing reforming, the space velocity, $C_1GSHSV$, typically ranges from about 1,000 to about 50,000.

In a preferred embodiment pressure swing reforming is conducted under bed packing and space velocity conditions that provide adequate heat transfer rates, as characterized by a heat transfer parameter, $\Delta T_{HT}$, of between about 0.1° C. to about 500° C., and more preferably between about 0.5° C. and 40° C. The parameter $\Delta T_{HT}$ is the ratio of the bed-average volumetric heat transfer rate that is needed for reforming, H, to the volumetric heat transfer coefficient of the bed, $h_v$. The volumetric heat transfer rate that is needed for reforming is calculated as the product of the space velocity with the heat of reforming (on heat per $C_1$ volume basis). For example, H=4.9 cal/cc/s=2.2 cal/cc*8000 $hr^{-1}$/3600 s/hr, where 2.2 cal/cc is the heat of reforming of methane per standard volume of methane, and 8000 is the $C_1GHSV$ of methane. When the duration of reform and regeneration steps are comparable, the value of H will be comparable in the two steps. The volumetric heat transfer coefficient of the bed, $h_v$, is known in the art, and is typically calculated as the product of a area-based coefficient (e.g. cal/cm$^2$s° C.) and a specific surface area for heat transfer ($a_v$, e.g. cm$^2$/cm$^3$), often referred to as the wetted area of the packing.

Bed packing materials suitable for use in the pressure swing reforming process include cordierite, aluminum silicate clays, mullite, silica-alumina, zirconia and the like that are stable to at least 1000° C.

Figure 2:
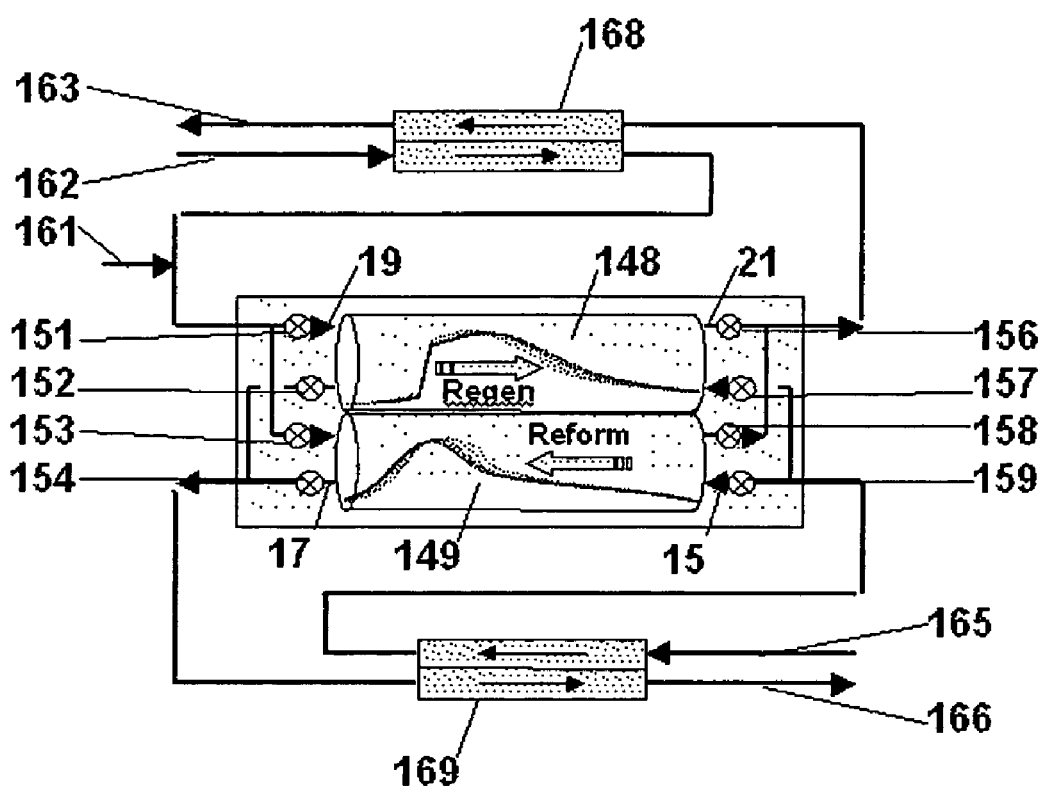
FIG. 2 is a schematic illustration of a basic two cycle pressure swing reforming process employing heat exchange.

FIG. 2 illustrates one embodiment of the process employing heat exchange. In this embodiment, two pressure swing reforming bed systems are used simultaneously such that one system is reforming while the other is regenerating. The use of multiple beds can provide a continuous flow of reformed product notwithstanding the cyclical operation of each bed. In FIG. 2, a first bed (148) is engaged in the step of regeneration, while a second bed (149) is engaged in the step of reforming. Each bed (148 and 149) includes both reforming and recuperating zones. In this embodiment, several sets of valves are used to control the various streams flowing to and from the beds. A first set of valves (157 and 159) controls the flow of hydrocarbon, steam and optional CO$_2$ feed to the beds, while a second set of valves (152 and 154) control the flow of the product of the reforming step exiting the recuperating zones. The third set of valves (151 and 153) regulate the flow of oxygen-containing gas/fuel and optional non-combusting gas to the beds and the fourth set of valves (156 and 158) control the flow of fluegas exiting the reforming zone.

In operation, when valves 151, 154, 156, and 159 are open, valves 152, 153, 157, and 158 are closed. With these valve states, oxygen containing gas (162) and fuel (161) enter the bed (148) through valve 151 while fluegas exits the bed (148) through valve 156. Concurrently, the hydrocarbon, steam and optional CO$_2$ feed enters the second bed (149) through valve 159 while the product of reforming exits this bed (149) through valve 154. At the conclusion of this step, valves 152, 153, 157 and 158 now open and valves 151, 154, 156 and 159 now close, and the cycle reverses, with the first bed (148) reforming the feed and the second bed (149) regenerating the heat.

Figure 3:
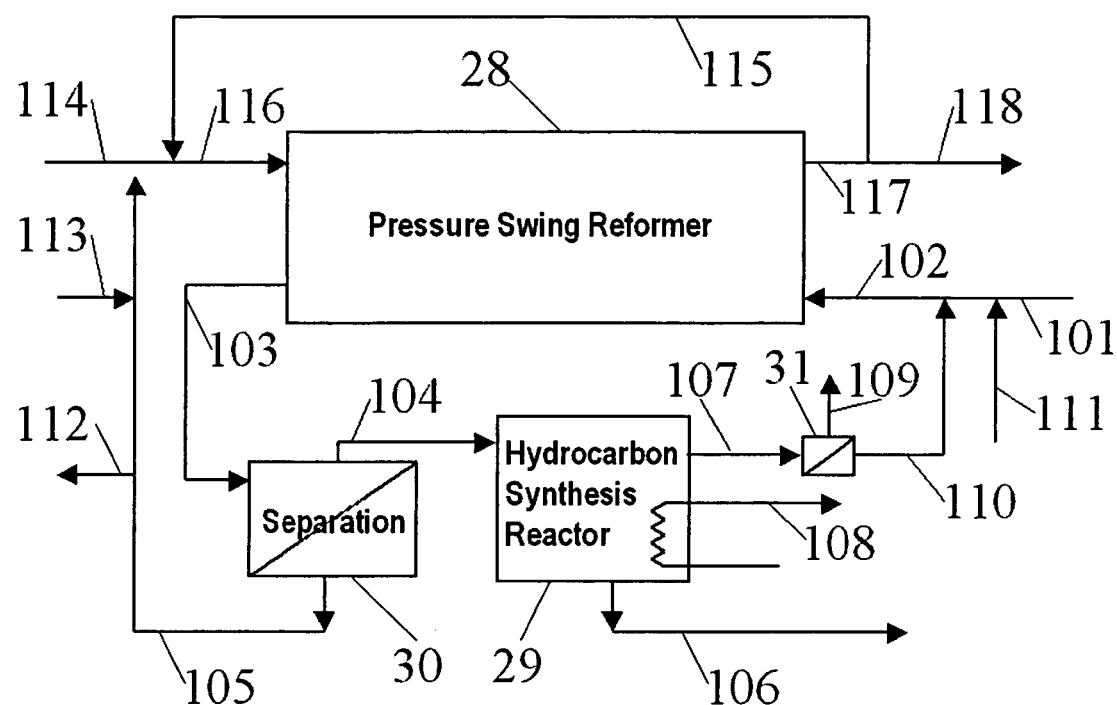
FIGS. 3 to 5 are schematic illustrations of a process designs employing pressure swing reforming and hydrocarbon synthesis.

Turning to FIG. 3, which illustrates an embodiment of the present invention, synthesis gas which is produced in the pressure swing reformer (28) is utilized in a hydrocarbon synthesis reactor (29) such as a Fischer-Tropsch (FT) reactor.

The pressure swing reforming process results in the formation of a syngas stream having a H$_2$:CO ratio of about 3:1. For gas conversion processes it is desirable to have a H$_2$:CO ratio of about 2:1. Therefore the syngas product of the pressure swing reforming process preferably is subjected to a separation step in which a fraction of the hydrogen is removed in a separator (30) for use in the regeneration step. Because the regeneration may be performed at substantially lower pressure than the reforming step a membrane separator is particularly preferred. As shown in FIG. 3, supplemental hydrocarbon, e.g., CH$_4$, may be added for fuel balance.

The pressure swing reforming reactor (28) is fed during its reforming step with a combined reforming feed (102), yielding a product syngas (103). During the regeneration step, the regeneration feed (116) enters the pressure swing reformer and fluegas product (117) is produced. The regeneration feed may enter together or as separate fuel and air streams, but is shown as a single combined feed (116) for material balance purposes. Heat exchange is not shown in FIG. 3, but is understood to take place as described in this disclosure and otherwise known in the art. Where conditions are given for streams (102, 103, 116, & 117), the conditions are at point of entry or departure of the pressure swing reformer.

The syngas product of reforming (103) has a higher H$_2$/CO than is needed for synthesis, and is directed to a separations step (30) where some of the excess H$_2$ is removed as stream (105). The remaining syngas (104), having H$_2$/CO suitable for synthesis, is directed to the hydrocarbon synthesis (HCS) reactor (29). In this example, the hydrocarbon synthesis reaction is catalyzed by a cobalt-based catalyst to produce a paraffinic liquid (106) at high conversion. Although this embodiment is shown as a single reactor, multiple reactors may be employed, as is known in the art. In addition, separation steps are included with the HCS reactor to segregate water and to keep the valuable, high-boiling components in the liquid stream (106) while placing the low-boiling components in a "tail-gas" stream (107). In the present example, the tail gas stream (107) includes all hydrocarbons with 4 carbons or fewer, the majority of which is methane. The HCS reaction is exothermic and thus heat is removed as a heated cooling medium (108). Cooling of HCS reactors is known in the art.

In the example shown, a fraction of the CO$_2$ in the HCS tail gas (107) is removed via separation (31), yielding a concentrated CO$_2$ stream (109) and a tailgas stream depleted in CO$_2$ (110). This tailgas stream (110) is a reduced-CO$_2$ HCS-tailgas, that is combined with fresh natural gas (101) and steam (111) to make the combined reforming feed (102). In this example, the steam includes a small amount of steam that is used to purge the pressure swing reformer bed of hydrocarbons and syngas at the end of the reforming step. It is understood that some compression is required in the syngas loop, as each of the steps extracts some pressure drop, such that the recycled syngas (110) will be at lower pressure than the reformer feed (102) in the absence of compression. Compression is least expensive if applied to the final tailgas (110), whose volume is the smallest.

Regeneration of the pressure swing reformer is carried out, in the present example, using primarily the hydrogen stream (105) that is removed in the hydrogen separator (30). In the general use of this invention, some of this hydrogen may be taken as a purified hydrogen stream (112) for use in other applications. For example, the H2 might be used in hydrocarbon upgrading steps. Also, in general, the heat of combustion of the hydrogen-containing stream (112) may not exactly match what is required for regeneration, and thus may require hydrogen purge (112) or supplemental fuel (113). The present example includes zero hydrogen removal (112) and a small amount of supplemental fuel (113). The combined regeneration feed (116) in the present example is composed of hydrogen fuel (105), a small amount of supplemental natural gas (113), fresh air (114) and recycled fluegas (115). Fluegas is recycled, in this embodiment, to reduce the oxygen content of the regeneration streams. The final tailgas emitted to atmosphere (118) is the regeneration product (117) minus the material recycled (115).

The material balance for this embodiment of the present invention is shown as a table of key streams in Table 2.

Figure 4:
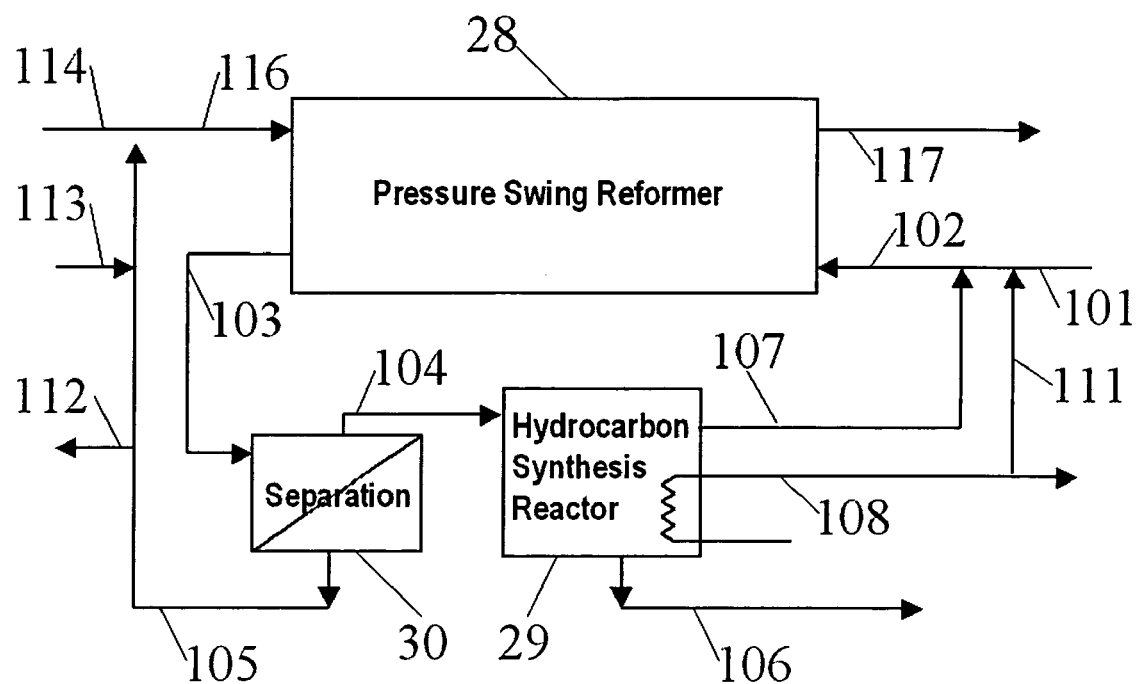

In yet another embodiment, byproducts and unconverted syngas is recycled, as shown in FIG. 4, to the pressure swing reformer without removal of any of the contained CO2. In addition, this embodiment uses excess air for regeneration, instead of the air/fluegas mixture of example 1, and this embodiment uses the steam generated in cooling the synthesis reactor directly as reactant for reforming.

The pressure swing reforming reactor (28) is fed during its reforming step with a combined reforming feed (102), yielding a product syngas (103). During the regeneration step, the regeneration feed (116) enters the pressure swing reformer and fluegas product (117) is produced. The regeneration feed may enter together or as separate fuel and air streams, but is shown as a single combined feed (116) for material balance purposes. Heat exchange is not shown in FIG. 4, but is understood to take place as described in this disclosure and otherwise known in the art. Where conditions are given for streams (102, 103, 116, & 117), the conditions are at point of entry or departure of the pressure swing reformer.

The syngas product of reforming (103) has a higher $H_2/CO$ than is needed for synthesis, and is directed to a separations step (30) where some of the excess $H_2$ is removed as stream (105). The remaining syngas (104), having $H_2/CO$ suitable for synthesis, is directed to the hydrocarbon synthesis (HCS) reactor (29). In this example, the hydrocarbon synthesis reaction is catalyzed by a cobalt-based catalyst to produce a paraffinic liquid (106) at high conversion. Although this embodiment is shown as a single reactor, multiple reactors may be employed, as is known in the art. In addition, separation steps are included with the HCS reactor to segregate water and to keep the valuable, high-boiling components in the liquid stream (106) while placing the low-boiling components in a "tail-gas" stream (107). In the present example, the tail gas stream (107) includes all hydrocarbons with 4 carbons or fewer, the majority of which is methane. The HCS reaction is exothermic and thus heat is removed as a heated cooling medium (108). In this embodiment, the cooling medium is water, which, upon absorbing heat from the HCS reaction, is converted to ~10 atm steam (108).

In the example shown, HCS-tailgas (107) is combined with fresh natural gas (101) and steam (111) to make the combined reforming feed (102). In this example, the source of the steam (111) is the steam (108) generated by cooling the HCS reactor. The amount of steam (111) used in pressure swing reforming includes a small amount of steam that is used to purge the pressure swing reformer bed of hydrocarbons and syngas at the end of the reforming step. It is understood that some compression is required in the syngas loop, as each of the steps extracts some pressure drop, such that the recycled syngas (110) will be at lower pressure than the reformer feed (102) in the absence of compression. Compression is least expensive if applied to the final tailgas (110), whose volume is the smallest.

Regeneration of the pressure swing reforming is carried out, in the present example, using primarily the hydrogen stream (105) that is removed in the hydrogen separator (30). In the general use of this invention, some of this hydrogen may be taken as a purified hydrogen stream (112) for use in other applications. For example, the H2 might be used in hydrocarbon upgrading steps. Also, in general, the heat of combustion of the hydrogen-containing stream (112) may not exactly match what is required for regeneration, and thus may require hydrogen purge (112) or supplemental fuel (113). The present example includes zero hydrogen removal (112) and a small amount of supplemental fuel (113). The combined regeneration feed (116) in the present example is composed of hydrogen fuel (105), a small amount of supplemental natural gas (113), and fresh air (114). The final flue gas emitted to atmosphere is the regeneration product (117).

The material balance for this embodiment of the present invention is shown as a table of key streams in Table 3.

As is known, the Fischer-Tropsch process is exothermic and water is used to control the temperature with steam (108) being produced. As shown in FIG. 3, at least part of this steam (108), may be used in the reformer (28). As will be readily appreciated the steam produced in cooling the hydrocarbon synthesis reactor may be at a lower pressure than the desired reforming pressure of the pressure swing reformer in which event the pressure swing reformer will be operated at the pressure at which the steam is produced or the steam may be compressed to a higher pressure.

Figure 5:
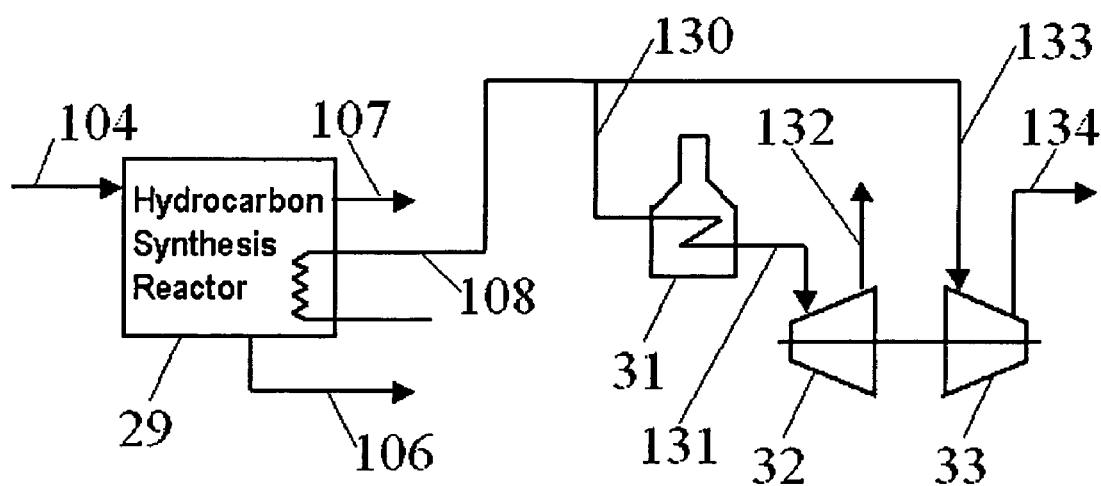

In yet another embodiment shown in FIG. 5 steam (108) recovered from the hydrocarbon synthesis reactor (29) is utilized to provide the power needed to compress the steam for the syngas reactor. In this embodiment, low pressure steam (108) from the hydrocarbon synthesis reactor is divided between a stream (130) to be expanded and a stream (133) to be compressed. In this embodiment the stream to be expanded is heated in a superheater (135) before expanding in a turbine (32) to produce shaft power. The shaft power turns compressor (33), which compresses steam (133) to become a higher pressure stream (134) that may be used in the reforming step.

In a preferred embodiment, the bed packing material in the pressure swing reformer is designed so that regeneration can be carried out with a pressure drop of less than 2 atm, more preferably less than 1 atm. Preferred packing materials for this embodiment are designed to pass large quantities of gas with small pressure drops. Preferred material shapes include honeycomb monoliths and wall-flow monoliths. Honeycomb monoliths are well known in the art, for example, as described in U.S. Pat. No. 3,885,977. Honeycomb monoliths derive their low pressure drop from the long straight channels oriented in the direction of flow. Wall-Flow monoliths are also known in the art, for example, as described in U.S. Pat. No. 4,276,071. Most commonly, wall flow monoliths are fabricated as derivatives of honeycomb monoliths, by plugging alternate channel ends, as described in U.S. Pat. No. 4,509,966. Wall-Flow monoliths derive their low pressure drop from the long straight channels oriented in the direction of flow, but add a large measure of heat transfer area by forcing the flow through the thin walls of the monolith.

The advantage of using a honeycomb or wall-flow monolith in the present invention is that, for a given level of heat transfer, these shapes can be operated at a much higher velocity than would be possible with a bed of particulate packing. Hydrocarbon synthesis processes are economically favored by operations at very large scale. At very large scale, reforming volume must also be large. It is desirable to provide this volume by increasing bed volume in all dimensions; diameter and length, thus providing the most economical bed designs. Since pressure drop increases with length, the very largest scales require the lowest pressure-drop designs. Preferred honeycomb monoliths for the present invention will have channel densities that range from about 100 cells/in$^2$ to about 1600 cells/in$^2$ (15–250 cells/cm$^2$).

TABLE 2

Flow Rates (kg/hr) and PSR Conditions for Selected Key Streams in FIG. 3 and Example 1.

| Stream | Fresh NG 101 | Ref Fd 102 | Ref Prod 103 | Regen Fd 116 | Regen Out 117 | Adj. SG (dry basis) 104 | HCS Liq. 106 | HCS Tailgas (dry basis) 107 | RCY Tailgas (dry basis) 110 |
|---|---|---|---|---|---|---|---|---|---|
| PSR P, atm | | 25 | 25 | 2.5 | 2 | | | | |
| PSR T, °C. | | 400 | 435 | 400 | 500 | | | | |
| NG (C1–C4) | 312,722 | 344,096 | 5,166 | 2,985 | 0 | 5,166 | | 31,374 | 31,374 |
| H2O | | 916,474 | 434,564 | 1,086,422 | 1,574,780 | | | | |
| H2 | | 4,724 | 134,126 | 44,173 | 0 | 89,942 | | 4,724 | 4,724 |
| CO | | 29,838 | 596,769 | 0 | 0 | 596,769 | | 29,838 | 29,838 |
| CO2 | | 98,327 | 136,177 | 23,280 | 31,488 | 136,177 | | 136,177 | 98,327 |
| N2 | | | | 4,657,947 | 4,651,855 | | | | |
| O2 | | | | 367,115 | 4,600 | | | | |
| Liquids (C5+) | | | | | | | 262,304 | | |

TABLE 3

Flow Rates (kg/hr) and PSR Conditions for Selected Key Streams in FIG. 4 and Example 2.

| Stream | Fresh NG 101 | Ref Fd 102 | Ref Prod 103 | Regen Fd 116 | Regen Out 117 | Adj. SG (dry basis) 104 | HCS Liq. 106 | RCY Tailgas (dry basis) 107 |
|---|---|---|---|---|---|---|---|---|
| PSR P, atm | | 10 | 10 | 1.4 | 1 | | | |
| PSR T, °C. | | 350 | 380 | 350 | 475 | | | |
| NG (C1–C4) | 59,618 | 66,866 | 2,006 | 4,064 | 0 | 2,006 | | 7,248 |
| H2O | | 128,429 | 47,226 | 0 | 83,157 | | | |
| H2 | | 945 | 25,334 | 7,288 | 0 | 17,988 | | 945 |
| CO | | 5,968 | 119,354 | 0 | 0 | 119,354 | | 5,968 |
| CO2 | | 18,245 | 18,245 | 0 | 11,177 | 18,245 | | 18,245 |
| N2 | | | | 1,066,786 | 1,065,857 | | | |
| O2 | | | | 323,895 | 249,618 | | | |
| Liquids (C5+) | | | | | | | 52,461 | |

What is claimed is:

1. An improvement in hydrocarbon synthesis processes using synthesis gas stream concaimng $H_2$ and CO, the improvement comprising: (a) generating a synthesis gas stream in a pressure swing reformer whereby the synthesis gas stream contains greater than a 2:1 mole ratio of $H_2$:CO; (b) separating a portion of the hydrogen from the synthesis gas stream to provide a synthesis gas stream containing about a 2:1 mole ratio of $H_2$:CO; (c) introducing the synthesis gas stream of step (b) into a hydrocarbon synthesis reactor for conversion to liquid products therein; and (d) introducing at least part of the separated hydrogen into the pressure swing reactor as a fuel source.

2. The improvement of claim 1 including cooling the hydrocarbon synthesis reactor with water to produce steam.

3. The improvement of claim 2 including introducing the steam into the pressure swing reformer for reforming hydrocarbons therein.

4. The improvement of claim 2 herein a portion of the steam is used to power a compressor for compressing another portion of the steam to provide steam at a higher pressure than in the absence of compression.

5. The improvement of claim 1 including recovering unreacted synthesis gas and by products from the hydrocarbon synthesis reactor and recycling the recovered gas and by products to the pressure swing reformer.

6. A synthesis gas and hydrocarbon conversion process comprising: (a) introducing a feed stream comprising a hydrocarbon and steam through a first end of a first zone containing bed packing materials and a steam reforming catalyst to produce a product synthesis gas stream at a first pressure having a ratio of $H_2$:CO greater than 2:1; (b) passing at least a portion of the product to step (a) to a second zone containing bed packing materials, and transferring sensible heat from the product to the packing materials; (c) removing substantially all of the product from said second zone; (d) introducing an oxygen-containing gas into the second end of said second zone; (e) contacting said oxygen-containing gas with a fuel and combusting said gas and fuel within said zones at a second pressure lower than the first pressure, thereby re-heating said first zone to reforming temperatures and creating a fluegas which exits through the first end of said first zone; (f) separating sufficient hydrogen from the product recovered in step (c) to produce a synthesis gas stream having a $H_2$:CO ratio of about 2:1; (g) introducing the synthesis gas of step (f) into a hydrocarbon synthesis reactor for conversion therein to liquid products; and (h) using separated hydrogen from step (f) as fuel in step (e).

7. The process of claim 6 including recovering unreacted synthesis gas and by products from the hydrocarbon synthesis reactor and recycling them to step (a).

8. The process of claim 6 including cooling the hydrocarbon synthesis reactor with water to produce steam and introducing the steam in step (a).

9. The process of claim 8 wherein a portion of the steam is used to power a compressor for compressing another portion of the steam to provide steam at a higher pressure for introduction into step (a).

10. The process of claim 6 including heat exchanging the oxygen containing gas of step (d) with the flue gas of step (e) before introducing the oxygen containing gas into the first end of said second zone.

* * * * *